United States Patent [19]

Shen et al.

[11] Patent Number: 4,731,465

[45] Date of Patent: Mar. 15, 1988

[54] PROCESS FOR PRODUCING NITRILOTRIACETONITRILE

[75] Inventors: Chung Y. Shen, St. Louis, Mo.; Kent P. Lannert, Freeburg, Ill.

[73] Assignee: Monsanto Company, St. Louis, Mo.

[21] Appl. No.: 586,876

[22] Filed: Mar. 7, 1984

Related U.S. Application Data

[63] Continuation of Ser. No. 413,058, Aug. 30, 1982, abandoned.

[51] Int. Cl.$^4$ .......................................... C07C 120/00
[52] U.S. Cl. ...................................................... 558/346
[58] Field of Search ................. 260/465.5 A; 558/346

[56] References Cited

U.S. PATENT DOCUMENTS

| | | | |
|---|---|---|---|
| 3,463,805 | 8/1969 | Morgan | 260/465.5 |
| 3,515,742 | 6/1970 | Morgan | 260/465.5 |
| 3,840,581 | 10/1974 | Neumaier | 260/465.5 A |
| 3,856,844 | 12/1974 | Wikman | 260/465.5 |
| 3,907,858 | 9/1975 | Davis | 260/465.5 A |
| 3,925,448 | 12/1975 | Lanier | 260/465.5 A |
| 3,950,384 | 4/1976 | Neumaier | 260/465.5 A |
| 3,959,342 | 5/1976 | Homberg | 260/465.5 A |
| 3,984,453 | 10/1976 | Chamberek | 260/465.5 A |

*Primary Examiner*—Joseph P. Brust
*Attorney, Agent, or Firm*—J. Beusen; R. Loyer; A. Hoffman

[57] ABSTRACT

A continuous process for preparing nitrilotriacetonitrile in which the reactants, formaldehyde, hydrogen cyanide, and either ammonia or hexamethylenetetramine are reacted first in a mixing reactor, preferably a circulating loop reactor at from about 90° C. to about 120° C., then reacted in a plug flow tubular reactor at from about 95° C. to about 120° C., then after cooling the reaction mixture crystalline nitrilotriacetonitrile is recovered.

12 Claims, 1 Drawing Figure

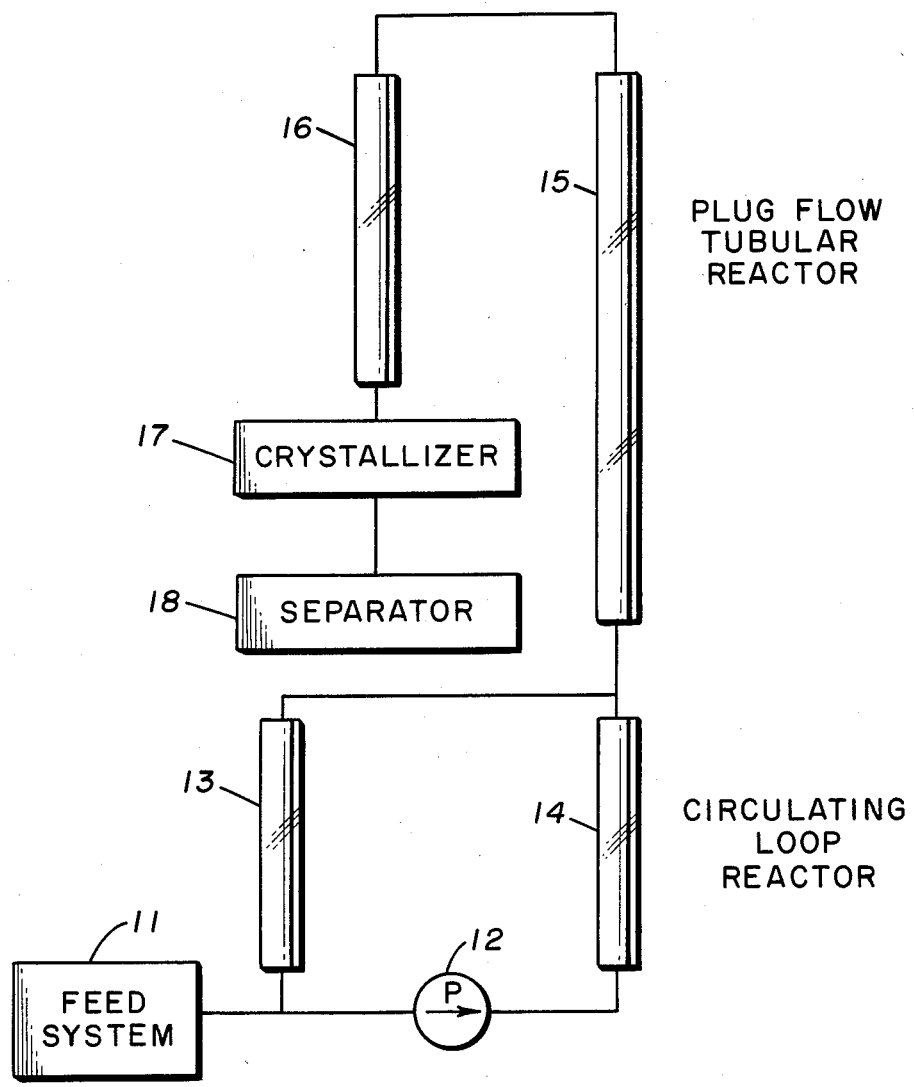

PROCESS FOR PRODUCING NITRILOTRIACETONITRILE

This is a continuation of application Ser. No. 413,058, filed Aug. 30, 1982, now abandoned.

BACKGROUND OF THE INVENTION

1. Field of the Invention

This invention relates to the continuous production of nitrilotriacetonitrile.

2. Background

It is well known that an amine will react with formaldehyde and hydrogen cyanide to produce an aminonitrile. Nitrilotriacetonitrile can be produced from hexamethylenetetramine by the following reaction:

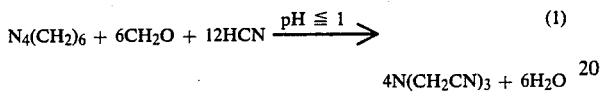

Nitrilotriacetonitrile can be produced from ammonia or a soluble ammonium salt such as ammonium sulfonate by the following reaction:

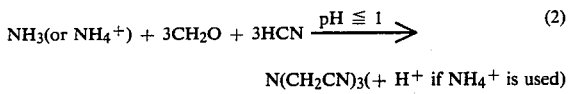

The rate of formation of nitrilotriacetonitrile increases with increased temperature. The reactions are highly exothermic.

The nitrilotriacetonitrile can be hydrolyzed to produce nitrilotriacetate. Nitrilotriacetate, normally as one of its water soluble salts, is used as a builder in detergent formulations.

Nitrilotriacetonitrile has been produced commercially in a batch process. However, three types of continuous processes have been disclosed in the patent literature.

U.S. Pat. No. 3,907,858 discloses a continuous process in which the reactants are brought together in a tubular plug-flow reactor under pressure, preferably autogenous pressure, of 5 to 100 psig at a temperature of at least 120° C. The tubular plug-flow design was used to minimize backmixing.

Increased temperatures can cause at least two problems. First, the corrosive character of the reaction mixture increases with temperature, causing damage to the reactor and to its control systems. Second, the rate at which acidic hydrolysis of the nitrilotriacetonitrile occurs increases with temperature causing reduction of the yield. These problems become more pronounced above 120° C.

U.S. Pat. No. 3,463,805 discloses a substantially adiabatic process for production of nitrilotriacetonitrile in which the reaction is permitted to exotherm producing a temperature rise of 50° C. to 100° C. from an initial temperature of 0° C. to 130° C., and an autogenous pressure rise of 1 to 3 atmospheres. The actual temperatures and pressures depend upon a number of factors, including the concentration of the reactants. A continuous process is disclosed in which this adiabatic process takes place as the reactants are pumped through an elongated reaction zone contained in an insulated reactor. The only system described uses a coiled stainless steel tubular reactor. U.S. Pat. No. 3,515,742 discloses an improvement in this adiabatic process in which heat is removed from the reacted reaction mixture by means of a heat exchanger. The heat so removed is then used to heat the reactants prior to their entry into the insulated reaction zone.

In an adiabatic process, the actual temperature and pressure rises during the reaction are determined by the temperature, concentrations, and rates of flow of the reactants entering the reactor. In order to attain a steady state temperature and pressure, these variables must be controlled very precisely. The normal fluctuations of these variables that occur during production can easily cause an upset of the delicately balanced temperature and pressure. Undesirable increases in temprature and pressure result in an increased rate of reaction, which in turn produces a further temperature increase. This self-reinforcing temperature cycle can cause the temperature and pressure to overshoot the desirable range. The disadvantages related to higher temperatures are discussed above. Additionally, broad fluctuations in temperature and pressure can pose a safety problem. The adiabatic process also can produce inconsistent results due to the lack of adequate control of the process.

U.S. Pat. No. 3,925,448 discloses production of nitrilotriacetonitrile from ammonium sulfate, formaldehyde, and hydrogen cyanide in a multistep process. The ammonium sulfate and formaldehyde are combined in a forming operation at the desired ratio, in a pump recirculation loop. The hydrogen cyanide is added in a second stage recirculating loop reactor at 93° C. which is kept full and under pressure to eliminate hydrogen cyanide vapor. This was followed by a third stage storage reaction step. The yield in the Example was 90%, but this required a reaction time of 1 to 1.5 hours.

In the processes discussed above, the reactants are heated to the desired operating temperature by a combination of the hot surfaces of the reactors and heat exchangers and the heat of reaction. This results in a heating period which requires additional reactor space to accomplish. During this heating period, intermediates such as methylenebisiminodiacetonitrile are produced. Methylenebisiminodiacetonitrile can be converted to nitrilotriacetonitrile, but this conversion proceeds slowly, requiring additional reaction time to accomplish.

An object of this invention is a continuous process to produce nitrilotriacetonitrile.

A further object of this invention is a continuous process to produce nitrilotriacetonitrile in which temperature and pressure can readily be controlled, with a minimum of heat transfer.

A further object to this invention is a continuous process to produce nitrilotriacetonitrile in which the formation of byproducts and intermediates is inhibited.

Still further objects of this invention will be apparent from the discussion below.

SUMMARY OF THE INVENTION

This invention provides a process for producing nitrilotriacetonitrile, comprising:

a. combining hexamethylenetetramine, or equivalent quantities of formaldehyde and ammonia or an ammonium salt, with formaldehyde and hydrogen cyanide in the presence of a mineral acid to form a reaction mixture for best results with $pH \leq 1$;

b. reacting said reaction mixture at from 90° C. to 120° C. in a mixing reactor such as a circulating loop;
c. further reacting said reaction mixture in a plug-flow tubular reactor at from 95° C. to 120° C.;
d. cooling said reaction mixture to form crystalline nitrilotriacetonitrile; and
e. separating said crystalline nitrilotriacetonitrile from the cooled reaction mixture.

BRIEF DESCRIPTION OF THE DRAWING

The drawing is a schematic representation of the process of this invention as it was carried out in the laboratory.

DESCRIPTION OF THE PREFERRED EMBODIMENT

This invention can utilize as a reaction mixture either (a) ammonia or an equivalent ammonium salt together with formaldehyde and hydrogen cyanide in the presence of a strong mineral acid preferably sulfuric acid, or (b) hexamethylenetetramine together with formaldehyde and hydrogen cyanide in the presence of a strong mineral acid preferably sulfuric acid. Additionally, mother liquor from crystallization and separation of nitrilotriacetonitrile can be recycled as part of the reaction mixture.

These reactants may be premixed in one feed tank and kept cold to minimize premature reaction. Alternatively, the reactants may be maintained in two or more feed tanks and premixed to form the reaction mixture just prior to introduction into the reactor system, to minimize premature reaction. For example, one feed tank could contain hexamethylenetetramine, formaldehyde, and water, while a second feed tank could contain hydrogen cyanide, sulfuric acid, recycled nitrilotriacetonitrile mother liquor, and water. Other combinations of the reactants in multiple feed tanks are also contemplated and can be used in this invention.

The reactants can be present in stoichiometric quantities, according to equations (1) or (2) above, or one or more of the reactants can be present in excess quantity. If hexamethylenetetramine, ammonia, or ammonium salt is the limiting reactant, formaldehyde and hydrogen cyanide each can be present up to 40%, preferably less than 10%, in excess of stoichiometric quantities. In order to minimize handling of dangerous waste streams, hydrogen cyanide may be used as the limiting reactant, with formaldehyde present up to 40% in excess as above, and with hexamethylenetetramine, ammonia or ammonium salt present up to 20% in excess of stoichiometric quantities.

After the reactants are combined, this reaction mixture is reacted in a two stage reactor system constructed of corrosion resistant materials, such as stainless steel. The first stage is a mixing reactor and the second stage is a plug-flow tubular reactor.

In the first stage, any reactor can be used in which the incoming reactants are mixed with the partially reacted reaction mixture, including but not limited to a stirred tank, or preferably a circulating loop reactor. The circulating loop reactor is a tubular reactor arranged in a continuous loop and fitted with a pump to circulate the reaction mixture around the continuous loop, with an inlet through which reactants are introduced into the circulating reaction mixture, with an outlet from which a portion of the circulating reaction mixture can be withdrawn, and with a temperature control means. The preferred temperature control means is a jacket surrounding a substantial portion of the continuous loop through which heat transfer liquid is circulated. After the circulating loop reactor has been filled for continuous operation, the rate of introduction of the reaction mixture must equal the rate of withdrawal of the reaction mixture in order to keep the reactor full and to maintain pressure within the desired limits. The rate of circulation of the reaction mixture around the continuous loop must be greater than the rate of introduction of the reaction mixture in order to obtain adequate mixing of the cold incoming reaction mixture with the hot circulating reaction mixture. Preferably the recirculation rate should be greater than five times the introduction rate of new reactant mixture. This mixing results in the cold incoming reaction mixture being instantaneously heated to the desired operating temperature of the reactor. The instantaneous heating inhibits the formation of methylenebisiminodiacetonitrile. The heat produced by the reaction that occurs in the first stage should be from 70% to 130% of the heat required to raise the temperature of the incoming reactants to the operating temperature of the first stage.

The reaction mixture withdrawn from the circulating loop reactor is then introduced into a plug-flow tubular reactor, preferably packed to minimize backmixing and to improve uniformity and fitted with a temperature control means, preferably a jacket through which a heat transfer fluid is circulated.

The temperature of the reaction mixture in the first stage must be kept above about 90° C., and the temperature in the second stage must be kept above about 95° C., to prevent crystallization of the nitrilotriacetonitrile in the reactor and connecting lines. The temperature should not be above 120° C. to minimize corrosive effects of the highly acidic reaction mixture and to minimize acidic hydrolysis of the nitrilotriacetonitrile. The temperature of both of the reactors must be maintained within these ranges, however, the temperatures of the reactors may differ from each other. Due to variations in temperature of the incoming reaction mixture, concentration of reactants, rate of introduction into the reactor, and other factors, the heat produced by the reaction may be either less than or more than the amount of heat necessary to raise the temperature of the incoming reaction mixture to the operating temperature of the circulating loop reactor. As a result, the means for regulating the temperature of the reactors must be capable of either adding or removing the heat required to maintain the temperature within the desired range.

The pressure of the reactor system should be maintained to minimize vaporization of the reaction mixture, particularly the hydrogen cyanide. Preferably this pressure should be maintained above about 20 psig (about 240 KPa) more preferably in the range of about 50 to about 100 psig, (about 450 KPa to about 790 KPa) and even more preferably about 75 psig, (about 620 KPa).

The sojourn time of the reaction mixture within the reactor system can be adjusted as desired, but preferably should be from about 7 to about 20 minutes total time in both reactors. The sojourn time is the total volume of the reactor system divided by the rate of addition of the reactants.

After the reaction mixture has passed through both reactors, it is cooled, preferably below 80° C. to form crystalline nitrilotriacetonitrile, which can then be separated from the mother liquor by conventional methods.

The mother liquor may be recycled as part of the reaction mixture as outlined above.

The following examples will further explain the process of this invention. They are meant to be illustrative only and are not intended to in any way limit the scope of this invention.

EXPERIMENTAL APPARATUS

The Examples utilized an apparatus following the schematic FIG. 1. Components were made using stainless steel. The feed system, 11, pumped the reaction mixture from feed tanks at the desired rate. The feed system for each group of Examples is described in greater detail below.

The circulating loop reactor consisted of a pump, 12, who shell and tube heat exchangers, 13 and 14, and connecting lines forming a continuous loop. The pump was operated at 100–150 ml/min. One heat exchanger was 5 inches (12.7 cm) in length, and the other was 7 inches (17.8 cm) in length. Both were constructed of ¼" (6.4 mm) tubing that was jacketed for heat transfer fluid. Flow of the heat transfer fluid was thermostatically controlled to maintain the desired temperature. The volume of the circulating loop reactor was 10 ml.

The plug-flow tubular reactor consisted of two sections, a packed section, 15, and a heated return section, 16. The packed section was also a shell and tube heat exchanger, made using 2 feet (61 cm) of ½" (12.7 mm) OD tubing, packed with glass beads, and jacketed for heat transfer fluid. The volume of the packed section was 30 ml. The heated return was another shell and tube heat exchanger, constructed of ⅛" and (3.2 mm) OD tubing with a jacket. The volume of the heated return was 5 ml, for a total reactor system volume of 45 ml. The packed section and heated return section were both supplied with a heat transfer fluid, the flow of which was thermostatically controlled to maintain the desired temperature. The tubes connecting the packed section, heated return, and the crystallizer were wrapped with heating tape to insure that the temperature remained above 95° C. to prevent pluggage caused by crystallized nitrilotriacetonitrile.

The crystallizer, 17, was a stirred receiver, cooled by a bucket of ice and water, and fitted with a valve at the bottom to remove the nitrilotriacetonitrile slurry produced by the process. Crystalline nitrilotriacetonitrile was separated by filtration, 18.

The reactors and the receiver were all maintained in a nitrogen atmosphere and at a pressure of about 75 psig (about 620 KPa).

EXAMPLES 1–13

In Examples 1–13 a single feed system was used. The single feed system consisted of a feed tank adapted to be cooled in a bucket of ice water, with a feed pump.

The reaction mixtures used in Examples 1–11 were based upon the following:

56 g 99.7% hexamethylenetetramine (HMTA)
204 g 35.9% $CH_2O$
22 g 96.4% $H_2SO_4$
133 g 99% HCN
127 g mother liquor (containing 9.23% $H_2SO_4$)
43 g $H_2O$ This results in a 1.5% excess of both formaldehyde and hydrogen cyanide. Minor adjustments were made to produce reaction mixtures shown in Table I.

In Examples 12 and 13, the mother liquor was not added. In Example 12, the molar ratio of $H_2SO_4$ to HMTA was 0.49, and in Example 13, it was 0.79, compared to 0.84 in the general recipe above. This lower level of acid had an adverse effect on the yield, but the process operated using this more concentrated reaction mixture.

The yield of the nitrilotriacetonitrile (NTAN) is shown in Table I for Examples 1–13. The temperature of the heat transfer fluid circulating through both of the reactors is shown as the jacket temperature, and the peak temperature of the reaction mixture as the reaction mixture left the circulating loop reactor is also shown.

EXAMPLES 14–19

Examples 14–19 utilized a dual feed system consisting of two feed tanks and two feed pumps. The feed from the two pumps joined at a tee. A small gear pump and mixing loop premixed the reactants to form the reaction mixture just prior to introduction into the circulating loop reactor. The solutions in the two feed tanks consisted of the following:

| Feed No. 1 | Feed No. 2 |
|---|---|
| 56 g 99.7% HMTA | 23 g 96.4% $H_2SO_4$ |
| 211 g 35.9% $CH_2O$ | 131 g mother liquor (9.23% $H_2SO_4$) |
| 9 g $H_2O$ | 36 g $H_2O$ |
| | 138 g 99% HCN |

The feed rates were adjusted to produce the amount of excess hydrogen cyanide indicated in Table I. Formaldehyde was present in 5% excess.

The yield of the nitrilotriacetonitrile (NTAN) produced in Examples 14–19 along with the operating conditions are shown in Table II. The temperature of the heat transfer fluid circulating through both of the reactors is shown as the jacket temperature. The temperature of the reaction mixture was measured as the reaction mixture left the circulating loop reactor, and the peak temperature at this point is shown.

TABLE I

| Example No. | HMTA | % Excess $CH_2O$ | HCN | Jacket Temp. °C. | Sojourn Time, Mins. | Reaction Mixture Temp. °C. | % Yield NTAN | Melting Range NTAN |
|---|---|---|---|---|---|---|---|---|
| 1 | — | 1.5 | 1.5 | 100 | 9.0 | — | 89.1 | |
| 2 | — | 1.5 | 1.5 | 100 | 10.2 | — | 91.6 | |
| 3 | — | 1.5 | 1.5 | 100 | 7.5 | 102 | 89.6 | |
| 4 | — | 1.5 | 1.5 | 100 | 14.9 | 98 | 90.9 | |
| 5 | — | 1.5 | 1.5 | 110 | 9.0 | 108 | 90.6 | |
| 6 | — | 1.5 | 1.5 | 115 | 9.0 | 113 | 90.9 | |
| 7 | — | 10.0 | 10.0 | 115 | 10.1 | 112 | 96.4 | |
| 8 | — | — | — | 115 | 10.0 | 111 | 90.8 | 124.5–126.2 |
| 9 | 3.4 | — | 3.4 | 115 | 10.0 | 112 | 92.0 | 125.0–126.3 |

TABLE I-continued

| Example No. | HMTA | % Excess CH₂O | HCN | Jacket Temp. °C. | Sojourn Time, Mins. | Reaction Mixture Temp. °C. | % Yield NTAN | Melting Range NTAN |
|---|---|---|---|---|---|---|---|---|
| 10 | — | 10.0 | 10.0 | 100 | 10.0 | 97 | 95.2 | 125.4–126.8 |
| 11 | — | 5.0 | 5.0 | 100 | 10.0 | 98 | 92.6 | 125.1–126.4 |
| 12 | — | 1.5 | 2.1 | 100 | 9.6 | — | 66.8 | |
| 13 | — | 5.0 | 5.0 | 100 | 9.6 | — | 91.7 | |

TABLE II

| Example No. | % Excess CH₂O | HCN | Jacket Temp. °C. | Sojourn Time, Mins. | Reaction Mixture Temp. °C. | % Yield NTAN | Melting Range NTAN |
|---|---|---|---|---|---|---|---|
| 14 | 5.0 | 11.0 | 115 | 10.2 | 113 | 91.6 | 125.5–127.2 |
| 15 | 5.0 | 0.8 | 115 | 10.0 | 113 | 88.0 | 125.0–126.8 |
| 16 | 5.0 | 4.7 | 115 | 10.0 | 113 | 91.5 | 125.5–127.3 |
| 17 | 5.2 | 10.6 | 115 | 10.3 | 113 | 92.6 | 125.0–126.8 |
| 18 | 5.0 | 10.4 | 115 | 10.4 | 113 | 91.3 | 125.3–127.9 |
| 19 | 5.0 | 16.5 | 115 | 10.6 | 113 | 97.5 | 125.4–127.0 |

EXAMPLE 20

In Example 20, a single feed system was used. The reaction mixture consisted of the following:
27 g NH₃
300 g 50% CH₂O
38 g 97.3% H₂SO₄
139 g 98% HCN
142 g mother liquor (containing 8.5% H₂SO₄)
This results in a 4.8% excess of formaldehyde and a 5.9% excess of hydrogen cyanide. The circulating loop reactor was thermostatically maintained at 114° C. and the plug-flow tubular reactor was thermostatically maintained at 115° C. The sojourn time was 13 minutes. The resulting nitrilotriacetonitrile had a melting point range of 126°–128° C., and the yield was 92.3%.

EXAMPLES 21–28

For these Examples, a tubular reactor system was built and operated in a substantially adiabatic manner, to represent a process outside the scope of this invention. The first stage was a tubular preheater constructed of ⅛" (3.2 mm) OD tubing 2 feet (61 cm) in length, jacketed for heat transfer fluid. The second stage, also 2 feet (61 cm) in length was a ½" (12.7 mm) OD tube packed with perforated stainless steel column packing and jacketed for heat transfer fluid. The heated return was similar to the first stage. The heat transfer fluid was circulated in series through the heated return, the second stage, and the first stage in a direction counter to the flow of the reactants through the reactor system. The reaction mixture consisted of the following:
56 g 99.6% HMTA
207 g 35.4% CH₂O
20 g 96.4% H₂SO₄
133 g 99% HCN
130 g mother liquor (containing 10.5% H₂SO₄)
40 g H₂O
This was 1.8% excess of formaldehyde and 1.6% excess of hydrogen cyanide. The temperature of the reaction mixture was measured at the outlet of the preheater and the peak temperature at this point is shown. The jacket temperature was the temperature of the heat transfer fluid as it entered the reactor system. Table III shows the fluctuations in temperature of the reaction mixture, compared to the relatively controlled temperatures found in Tables I and II. Uncontrolled temperatures such as those shown in Table III can cause safety and process control problems. At temperatures above 120° C., corrosion problems increase causing damage to the reactor system and resulting in a product containing corrosion material. Additionally, if temperature variations are broad enough, decreases in yield can result.

TABLE III

| Example No. | Jacket Temp °C. | Sojourn Time, Mins. | Reaction Mixture Temp °C. | % Yield NTAN |
|---|---|---|---|---|
| 21 | 110 | 8.0 | 125 | 92.4 |
| 22 | 100 | 7.6 | 130 | 94.3 |
| 23 | 100 | 4.0 | — | 90.2 |
| 24 | 110 | 4.3 | 135 | 90.0 |
| 25 | 100 | 16.4 | 102 | 92.7 |
| 26 | 100 | 6.0 | 150 | 89.7 |
| 27 | 100 | 10.9 | 105 | 91.0 |
| 28 | 100 | 10.8 | 105 | 91.3 |

We claim:

1. A continuous process for producing nitrilotriacetonitrile, comprising:
   a. combining reactants, (1) hexamethylenetetramine or equivalent amounts of formaldehyde and ammonia or an ammonium salt, (2) formaldehyde, and (3) hydrogen cyanide with a mineral acid to form a reaction mixture;
   b. reacting said reaction mixture in a reactor in which the incoming reaction mixture is mixed with partially reacted reaction mixture, which reactor is maintained at about 90° C. to 120° C.;
   c. further reacting said reaction mixture in a plug-flow tubular reactor maintained at about 95° C. to about 120° C.;
   d. cooling said reaction mixture to form crystalline nitrilotriacetonitrile; and
   e. separating said crystalline nitrilotriacetonitrile from the cooled reaction mixture.

2. The process of claim 1 wherein the reactor in b. is a circulating loop reactor.

3. The process of claim 1 or 2 wherein the reactants in a. are hexamethylenetetramine, formaldehyde, and hydrogen cyanide.

4. The process of claim 1 or 2 wherein the reactants in a. are ammonia or an ammonium salt, formaldehyde, and hydrogen cyanide.

5. The process of claim 1 or 2 wherein the formaldehyde in a. is present up to 40% in excess of stoichiometric quantities.

6. The process of claims 1 or 2, wherein the hydrogen cyanide in a. is present up to 40% in excess of stoichiometric quantities.

7. The process of claim 1 or 2 wherein the hexamethylenetetramine, ammonia, or ammonium salt is present up to 20% in excess of stoichiometric quantities.

8. The process of claims 1 or 2, wherein the total sojourn time in steps b. and c. is from about 7 to about 20 minutes.

9. The process of claim 1 or 2, further comprising premixing two reactant solutions to form the reaction mixture just prior to the combining step a.

10. The process of claim 9, wherein one reactant solution comprises hexamethylenetetramine, formaldehyde, and water, and the other reactant solution comprises sulfuric acid, recycled mother liquor from nitrilotriacetonitrile crystallization, hydrogen cyanide, and water.

11. The process of claims 1 or 2, wherein reacting steps b. and c. are done at a pressure of about 50 to about 100 pounds per square inch gauge.

12. The process of claims 1 or 2 wherein the reaction mixture formed in a. has $pH \leq 1$.

* * * * *